United States Patent [19]

Hanada et al.

[11] Patent Number: 5,656,264
[45] Date of Patent: Aug. 12, 1997

[54] METHOD FOR PROMOTING HAIR GROWTH

[75] Inventors: Seigo Hanada; Shinji Yamamoto, both of Dazaifu, Japan

[73] Assignee: Sansyo Seiyaku Co., Ltd., Onojo, Japan

[21] Appl. No.: 394,217

[22] Filed: Feb. 24, 1995

Related U.S. Application Data

[63] Continuation of Ser. No. 104,608, Aug. 11, 1993, abandoned, which is a continuation of Ser. No. 942,188, Sep. 9, 1992, abandoned.

[30] Foreign Application Priority Data

Sep. 10, 1991 [JP] Japan .................................. 3-230630
Aug. 11, 1992 [JP] Japan .................................. 4-214405

[51] Int. Cl.$^6$ .............................. A61K 7/06; A61K 7/00
[52] U.S. Cl. .................................... 424/70.1; 514/880
[58] Field of Search ................ 424/70.1, 74; 514/880, 514/881

[56] References Cited

U.S. PATENT DOCUMENTS

| | | | |
|---|---|---|---|
| 3,497,307 | 2/1970 | Hitchings | 514/261 |
| 3,911,128 | 10/1975 | Buzzolini | 514/261 |
| 4,557,934 | 12/1985 | Cooper | 514/635 |
| 4,853,386 | 8/1989 | Friebe | 514/261 |
| 5,041,439 | 8/1991 | Kasting | 514/937 |
| 5,053,410 | 10/1991 | Grollier | 514/256 |
| 5,151,424 | 9/1992 | Clark | 514/261 |
| 5,164,394 | 11/1992 | Bolund | 514/261 |
| 5,182,269 | 1/1993 | Gazzani | 514/44 |

FOREIGN PATENT DOCUMENTS

| | | | |
|---|---|---|---|
| 51273/90 | 1/1990 | Australia . | |
| 0 387 757 | 9/1990 | European Pat. Off. . | |
| 1440795 | 4/1966 | France . | |
| 3210669 | 9/1983 | Germany . | |
| 2088366 | 5/1982 | United Kingdom | 514/261 |

OTHER PUBLICATIONS

Hair Agent Containing Cycle Adenosine Derivative, JP-63-88112 vol. 12 No. 316 (C-524) (3163) Aug. 26, 1988—Abstract.
Patent Abstracts of Japan, 58-88306(A), (Aug. 13, 1983) vol. 7, No. 185 p. 28 C 181.
Patent Abstracts of Japan, 59-27809 (A), (May 26, 1984) vol. 8, No. 114 p. 58 C 225.

*Primary Examiner*—Sallie M. Gardner
*Attorney, Agent, or Firm*—Armstrong, Westerman, Hattori, McLeland & Naughton

[57] ABSTRACT

A preparation for promoting hair growth is disclosed, which contains as an effective ingredient or ingredients one or more compounds selected from the group consisting of purine compounds, pyridylurea compounds, diphenylurea compounds, pyrimidine compounds, imidazole compounds, benzoylaminourea compounds and 4-substituted aminopyrrolo[2,3-d]pyrimidine compounds. This preparation exhibits an excellent effect of promoting hair growth or curing alopecia such as male alopecia or alopecia areata. Of the effective compounds, purine compounds and pyridyl compounds exhibit particularly remarkable effects.

1 Claim, No Drawings

METHOD FOR PROMOTING HAIR GROWTH

This application is a continuation of application Ser. No. 08/104,608 filed Aug. 11, 1993, now abandoned, which is a continuation of application Ser. No. 07/942,188, filed Sep. 9, 1992, now abandoned.

BACKGROUND OF THE INVENTION

This invention relates to a preparation for promoting hair growth containing, as an effective ingredient, a material showing remarkable effects of promoting hair growth and curing alopecia such as male alopecia or alopecia areata.

Many preparations for promoting hair growth have conventionally been used for prophylaxis or treatment of baldness and thinning of hair.

Ingredients contained in a preparation for promoting hair growth are generally intended to improve the circulation of the blood in scalp, attain cleaning, anti-inflammation and sterilization of scalp, activate enzymes of cells constituting hair follicles and surrounding tissue, improve energy metabolism of hair-matrix cells and depress the action of male sex hormone in scalp. For example, carpronium chloride, vitamin E, an extract of *Capsieum annuum L.*, an extract of Japanese chirata and a garlic extract have been intended to increase the amount of blood stream in hair follicles based on their vasodilative action on peripheral blood vessel, thereby to activate hair-matrix cells. Since alopecia is known to be induced by inflammation, anti-inflammatory agents such as glycyrrhizin and allantoin and germicides such as hinokitiol and resorcin have been used for preventing inflammation or production of decomposition products which might be produced by bacteria from scurf or sebum and which can induce inflammation. Vitamins such as vitamin A, vitamin B group, biotin and pantothenic acid derivatives have been used for activating enzymes of hair-matrix cells to promote synthesis of hair, pentadecanoic acid glyceride has been used for improving energy metabolism of hair-matrix cells, and female sex hormones such as estradiol and ethynylestradiol have been used for depressing the action of male sex hormone which is believed to be the primary cause of male alopecia.

However, all of these conventional ingredients contained in a preparation for promoting hair growth have failed to give a satisfactory result, though they exhibit a hair growth-promoting effect or an alopecia-preventing effect to some extent. In particular, they fail to exhibit an enough effect of promoting hair growth and curing alopecia.

With the above-described situation in mind, the inventors have made intensive investigations and, as a result, have found ingredients exhibiting a remarkable effect of promoting hair growth, thus having completed the invention.

SUMMARY OF THE INVENTION

It is an object of the present invention to provide a preparation for promoting hair growth which, when applied to scalp, exhibits a marked effect of promoting hair growth and curing male alopecia or alopecia areata.

Other objects, features and advantages of the present invention will become apparent from the detailed description of the preferred embodiments of the invention to follow.

DETAILED DESCRIPTION OF THE PREFERRED EMBODIMENTS OF THE INVENTION

The mechanism of how alopecia is induced has not yet been clarified in detail. However, main factors which are at present considered to induce alopecia are as follows:

1. Acatastasia of physiological functions of scalp;
2. Depression of metabolism function in hair follicles and hair bulb;
3. Depression of the function of hair follicles due to male sex hormone-action in sebaceous gland, hair follicles and hair root;
4. Mental stress; and
5. Others such as genetic factors and disease factors.

In addition, aging is believed to accelerate epilation and it is also believed that, as hair-matrix cells age, they suffer depression of cell division ability and cell differentiation ability and depression of every metabolic activity including blood stream amount in localized areas, leading to thinning of hair and epilation.

The preparation of the present invention for promoting hair growth is particularly effective for male alopecia and alopecia areata which are seemingly induced by depression of the function of hair follicles.

The effective ingredients contained in the preparation of the present invention are represented by the following general formulae (1) to (7):

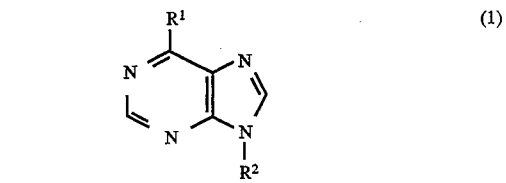

(1)

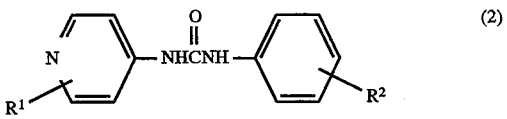

(2)

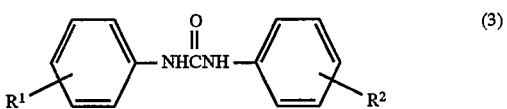

(3)

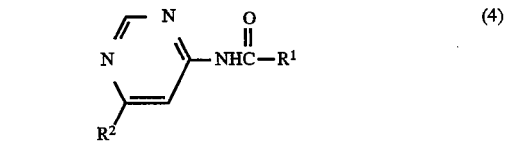

(4)

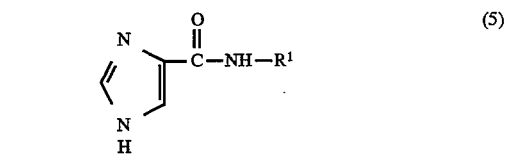

(5)

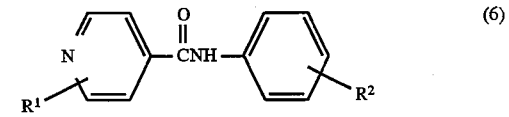

(6)

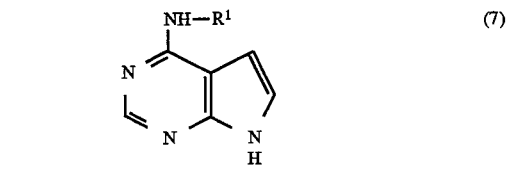

(7)

In the above general formula (1), examples of the substituent represented by $R^1$ include an alkyl group (containing 1 to 22, preferably 1 to 12, carbon atoms and being straight or branched; e.g., a methyl group, an ethyl group, a propyl group, an isopropyl group, a butyl group, an isobutyl group, a pentyl group, a hexyl group, a heptyl group, an octyl group, a nonyl group or a dodecyl group), a cyclic hydrocarbon group (e.g., a 2-cyclohexylethyl group, a cyclohexyl group, a cyclohexylmethyl group, a cyclopentyl group, a cyclopentylmethyl group or a 2-cyclopentylethyl group), an alkenyl group (containing 1 to 22, preferably 1 to 12, carbon atoms and being straight or branched; e.g., a vinyl group, an allyl group, a 2-butenyl group or an isoprenyl group), a substituted or non-substituted aralkyl group [a benzyl group (e.g., a benzyl group, a 2-methylbenzyl group, a 4-methylbenzyl group, a 4-ethylbenzyl group, a 3-chlorobenzyl group, a 4-fluorobenzyl group or a 4-nitrobenzyl group), a phenylethyl group (e.g., a phenylethyl group, a 2-methylphenylethyl group, a 4-methylphenylethyl group, a 4-ethylphenylethyl group, a 3-chlorophenylethyl group, a 4-fluorophenylethyl group, a 4-nitrophenylethyl group, a 4-propylphenylethyl group, a 3,5-difluorophenylethyl group, a 4-nitrophenylethyl group, a 2-cyanophenylethyl group, a 4-dimethylaminophenylethyl group, a 4-methoxyphenylethyl group, a 3-trimethylsilyloxyphenylethyl group, a 4-trifluoromethylphenylethyl group, a 4-butyldimethylsilyloxyphenylethyl group, a 2-methylthiophenylethyl group or a 4-trimethylsilyloxyphenylethyl group), a substituted or non-substituted styryl group (e.g., a styryl group, a 2-methylstyryl group, a 4-methylstyryl group, a 4-ethylstyryl group, a 3-chlorostyryl group, a 4-fluorostyryl group, a 4-nitrostyryl group, a 4-propylstyryl group, a 3,5-difluorostyryl group, a 4-nitrostyryl group, a 2-cyanostyryl group, a 4-dimethylaminostyryl group, a 4-methoxystyryl group, a 3-trimethyloxystyryl group, a 4-trifluoromethylstyryl group, a 4-butyldimethylsilyloxystyryl group, a 2-methylthiostyryl group or a 4-trimethylsilyloxystyryl group), an alkylamino group (represented by —NRR' wherein R and R' may be the same or different and each represents an alkyl group containing 1 to 22, preferably 1 to 12, carbon atoms and being straight or branched, such as a methyl group, an ethyl group, a propyl group, an isopropyl group, a butyl group, an isobutyl group, a pentyl group, an isopentyl group, a 3-methylpentyl group, a hexyl group, a 2-ethylhexyl group, a heptyl group, an octyl group, a nonyl group or a dodecyl group), an amino group having a cyclic hydrocarbon group (represented by —NH—R wherein R represents, for example, a 2-cyclohexylethyl group, a cyclohexyl group, a 3-cyclohexylpropyl group, a 2-cyclohexylpropyl group, a cyclohexylmethyl group, a cyclopentyl group, a cyclopentylmethyl group or a 2-cyclopentylethyl group), an alkenylamino group (represented by —NH—R wherein R represents an alkenyl group containing 1 to 22, preferably 1 to 12, carbon atoms and being straight or branched, such as a vinyl group, an allyl group, a 2-butenyl group, an isoprenyl group, a 3-methyl-2-butenyl group or a 3-ethyl-2-pentenyl group), a substituted or non-substituted benzylamino group (represented by —NH—R wherein R represents, for example, a benzyl group, a 2-methylbenzyl group, a 3-methylbenzyl group, a 4-methylbenzyl group, a 4-ethylbenzyl group, a 3-chlorobenzyl group, a 4-chlorobenzyl group, a 2,4-dichlorobenzyl group, a 2-hydroxybenzyl group, a 3-fluorobenzyl group, a 4-nitrobenzyl group, a 4-bromobenzyl group, a 4-fluorobenzyl group, a 3-nitrobenzyl group, a 4-propylbenzyl group, a 3,5-difluorobenzyl group, a 2-cyanobenzyl group, a 2-acetaminobenzyl group, a 4-acetaminobenzyl group, a 4-methoxycarbonylbenzyl group, a 4-dimethylaminobenzyl group, a 4-methoxybenzyl group, a 3-trimethylsilyloxybenzyl group, a 3-trifluoromethylbenzyl group, a 4-butyldimethylsilyloxybenzyl group, a 2-methylthiobenzyl group, a 4-trimethylsilyloxybenzyl group or a 4-methylthiobenzyl group), a substituted or non-substituted phenylethylamino group (represented by —NH—R wherein R represents, for example, a phenylethyl group, a 2-methylphenylethyl group, a 4-methylphenylethyl group, a 4-ethylphenylethyl group, a 3-chlorophenylethyl group, a 4-fluorophenylethyl group, a 4-nitrophenylethyl group, a 4-propylphenylethyl group, a 3,5-difluorophenylethyl group, a 3-nitrophenylethyl group, a 2-cyanophenylethyl group, a 4-dimethylaminophenylethyl group, a 4-methoxyphenylethyl group, a 3-trimethylsilyloxyphenylethyl group, a 4-trifluoromethylphenylethyl group, a 4-butyldimethylsilyloxyphenylethyl group, a 2-methylthiophenylethyl group or a 4-trimethylsilyloxyphenylethyl group), a substituted or non-substituted phenylamino group (represented by —NH—R wherein R represents, for example, a phenyl group, a 2-methylphenyl group, a 3-methylphenyl group, a 4-methylphenyl group, 4-ethylphenyl group, a 3-chlorophenyl group, a 4-chlorophenyl group, a 2,4-dichlorophenyl group, a 2-hydroxyphenyl group, a 3-fluorophenyl group, 4-nitrophenyl group, a 4-bromophenyl group, a 4-fluorophenyl group, a 3-nitrophenyl group, a 4-propylphenyl group, a 3,5-difluorophenyl group, a 2-cyanophenyl group, a 2-acetaminophenyl group, a 4-acetaminophenyl group, 4-methoxycarbonylphenyl group, a 4-dimethylaminophenyl group, a 4-methoxyphenyl group, a 3-trimethylsilyloxyphenyl group, a 4-trifluoromethylphenyl group, a 4-butyldimethylsilyloxyphenyl group, a 2-methylthiophenyl group, a 4-trimethylsilyloxyphenyl group or a 4-methylthiophenyl group), a substituted or non-substituted phenylaminocarbonylamino group (represented by —NH—R wherein R represents, for example, a phenylaminocarbonyl group, a 2-methylphenylaminocarbonyl group, a 3-methylphenylaminocarbonyl group, a 4-methylphenylaminocarbonyl group, a 4-ethylphenylaminocarbonyl group, a 3-chlorophenylaminocarbonyl group, a 4-chlorophenylaminocarbonyl group, a 2,4-dichlorophenylaminocarbonyl group, a 2-hydroxyphenylaminocarbonyl group, a 3-fluorophenylaminocarbonyl group, a 4-nitrophenylaminocarbonyl group, a 4-bromophenylaminocarbonyl group, a 4-fluorophenylaminocarbonyl group, a 2-cyanophenylaminocarbonyl group, a 2-acetaminophenylaminocarbonyl group, a 4-methoxycarbonylphenylaminocarbonyl group, a 4-dimethylaminophenylaminocarbonyl group, a 4-methoxyphenylaminocarbonyl group, a 3-trimethylsilyloxyphenylaminocarbonyl group, a 4-trifluoromethylphenylaminocarbonyl group, a 4-butylmethylsilyloxyphenylaminocarbonyl group, a 2-methylthiophenylaminocarbonyl group, a 4-trimethylsilyloxyphenylaminocarbonyl group or a 4-methylthiophenylaminocarbonyl group), a 4-hydroxy-3-methyl-2-butenyl group, a 4-acetoxy-3-methyl-2-butenyl group, a 4-propionyloxy-3-methyl-2-butenyl group, a 4-butyryloxy-3-methyl-2-butenyl group, a 2-chloro-5-methyl-1-pentenyl group, a 2-pyridyl group, a 2-pyridylmethyl group, a 3-pyridylmethyl group, a 4-pyridylmethyl group, a 2-pyrrolylmethyl group, a 4-oxazolylmethyl group, a 2-imidazolylmethyl group, a 3-pyridazyl group, a 3-pyridazylmethyl group, a 1-naphthyl group, a 1-naphthylmethyl group, a 2-naphthyl group and a 2-naphthylmethyl group, and examples of the substituent represented by $R^2$ include a hydrogen atom, a pentose residue (e.g., a 1-ribofuranosyl group, a 1-lyxofuranosyl group, a 1-xylofuranosyl group or a 1-arabofuranosyl group) and a hexose residue (e.g., a 1-glucosyl group, a 1-galactosyl group, a 1-gulosyl group, a 1-mannosyl group or a 1-allosyl group).

In the above general formula (2), examples of the substituents $R^1$ and $R^2$, which may be the same or different, include a hydrogen atom, an alkyl group having 1 to 6 carbon atoms, a chlorine atom, a hydroxy group, a fluorine atom, a nitro group, a bromine atom, a cyano group, an acetamino group, a methoxycarbonyl group, a dimethylamino group, a methoxy group, a trifluoromethyl group, a butyldimethylsilyloxy group, a methylthio group, a trimethylsilyloxy group, an acetoxy group, a propionyloxy group, a methylsulfinyl group, a methylsulfonyl group, a carboxyl group, a methoxycarbonyl group and an ethoxycarbonyl group.

In the above general formula (3), examples of the substituents $R^1$ and $R^2$, which may be the same or different, include a hydrogen atom, a methyl group, an ethyl group, a butyl group, a propyl group, a chlorine atom, a hydroxy group, a fluorine atom, a nitro group, a bromine atom, a cyano group, an acetamino group, a methoxycarbonyl group, a dimethylamino group, a methoxy group, a trimethylsilyloxy group, a trifluoromethyl group, a butyldimethylsilyloxy group, a methylthio group, an acetoxy group, a propionyloxy group, a methylsulfinyl group, a methylsulfonyl group, a carboxyl group, a methoxycarbonyl group and an ethoxycarbonyl group.

In the above general formula (4), examples of the substituent represented by $R^1$ include a substituted or non-substituted phenyl group (e.g., a phenyl group, a 2-methylphenyl group, a 3-methylphenyl group, a 4-methylphenyl group, a 4-ethylphenyl group, a 3-chlorophenyl group, a 4-chlorophenyl group, a 2,4-dichlorophenyl group, a 2-hydroxyphenyl group, a 3-fluorophenyl group, a 4-nitrophenyl group, a 4-bromophenyl group, a 4-fluorophenyl group, a 3-nitrophenyl group, a 4-propylphenyl group, a 3,5-difluorophenyl group, a 2-cyanophenyl group, a 2-acetaminophenyl group, a 4-acetaminophenyl group, a 4-methoxycarbonylphenyl group, a 4-dimethylaminophenyl group, a 4-methoxyphenyl group, a 3-trimethyloxyphenyl group, a 4-trifluoromethylphenyl group, a 4-butyldimethylsilyloxyphenyl group, a 2-methylthiophenyl group, a 4-trimethylsilyloxyphenyl group or a 4-methylthiophenyl group) and a substituted or non-substituted anilino group (e.g., an anilino group, a 2-methylanilino group, a 3-methylanilino group, a 4-methylanilino group, a 4-ethylanilino group, a 3-chloroanilino group, a 4-chloroanilino group, a 2,4-dichloroanilino group, a 2-hydroxyanilino group, a 3-fluoroanilino group, a 4-nitroanilino group, a 4-bromoanilino group, a 4-fluoroanilino group, a 3-nitroanilino group, a 4-propylanilino group, a 3,5-difluoroanilino group, a 2-cyanoanilino group, a 2-acetaminoanilino group, a 4-acetaminoanilino group, a 4-methoxycarbonylanilino group, a 4-dimethylaminoanilino group, a 4-methoxyanilino group, a 3-trimethylsilyloxyanilino group, a 4-trifluoromethylanilino group, a 4-butyldimethylsilyloxyanilino group, a 2-methylthioanilino group, a 4-trimethylsilyloxyanilino group or a 4-methylthioanilino group) and examples of the substituent represented by $R^2$ include a hydrogen atom, a methyl group, an ethyl group, a butyl group, a propyl group, a chlorine atom, a hydroxy group, a fluorine atom, a nitro group, a bromine atom, a cyano group, an acetamino group, a methoxycarbonyl group, a dimethylamino group, a methoxy group, a trimethyloxy group, a trifluoromethyl group, a butyldimethylsilyloxy group, a methylthio group, a trimethylsilyloxy group, an acetoxy group, a propionyloxy group, a methylsulfinyl group, a methylsulfonyl group, a carboxyl group, a methoxycarbonyl group and an ethoxycarbonyl group.

In the above general formula (5), examples of the substituent represented by $R^1$ include a substituted or non-substituted phenyl group (e.g., a phenyl group, a 2-methylphenyl group, a 3-methylphenyl group, a 4-methylphenyl group, a 4-ethylphenyl group, a 3-chlorophenyl group, a 4-chlorophenyl group, a 2,4-dichlorophenyl group, a 2-hydroxyphenyl group, a 3-fluorophenyl group, a 4-nitrophenyl group, a 4-bromophenyl group, a 4-fluorophenyl group, a 3-nitrophenyl group, a 4-propylphenyl group, a 3,5-difluorophenyl group, a 2-cyanophenyl group, a 2-acetaminophenyl group, a 4-acetaminophenyl group, a 4-methoxycarbonylphenyl group, a 4-dimethylaminophenyl group, a 4-methoxyphenyl group, a 3-trimethylsilyloxyphenyl group, a 4-trifluoromethylphenyl group, a 4-butyldimethylsilyloxyphenyl group, a 2-methylthiophenyl group, a 4-trimethylsilyloxyphenyl group or a 4-methylthiophenyl group).

In the above general formula (6), examples of the substituent represented by $R^1$ include a hydrogen atom, a 2-methyl group, a 3-methyl group, a 2-ethyl group, a 2-chloro atom, a 3-chloro atom, 2,6-dichloro atoms, a 2-hydroxy group, a 2-fluoro atom, a 2-nitro group, a 2-bromo atom, a 2-fluoro atom, a 3-nitro group, a 2-propyl group, 2,6-difluoro atoms, a 2-cyano group, a 2-acetamino group, a 3-acetamino group, a 2-methoxycarbonyl group, a 2-dimethylamino group, a 2-methoxycarbonyl group, a 2-dimethylamino group, a 2-methoxy group, a 2-trimethylsilyloxy group, a 2-trifluoromethyl group, a 2-butyldimethylsilyloxy group, a 2-methylthio group, a 2-trimethylsilyloxy group, a 2-methylthio group, a 2-acetoxy group, a 2-propionyloxy group, a 2-methylsulfinyl group, a 2-methylsulfonyl group, a 2-carboxyl group, a 2-methoxycarbonyl group and a 2-ethoxycarbonyl group, and examples of the substituent represented by $R^2$ include a hydrogen atom, a methyl group, an ethyl group, a butyl group, a propyl group, a chlorine atom, a hydroxy group, a fluorine atom, a nitro group, a bromine atom, a cyano group, an acetamino group, a methoxycarbonyl group, a dimethylamino group, a methoxy group, a trifluoromethyl group, a butyldimethylsilyloxy group, a methylthio group, a trimethylsilyloxy group, an acetoxy group, a propionyloxy group, a methylsulfinyl group, a methylsulfonyl group, a carboxyl group, a methoxycarbonyl group and an ethoxycarbonyl group.

In the above general formula (7), examples of the substituent represented by $R^1$ include a benzyl group (e.g., a benzyl group, a 2-methylbenzyl group, a 3-methylbenzyl group, a 4-methylbenzyl group, a 4-ethylbenzyl group, a 3-chlorobenzyl group, a 4-chlorobenzyl group, a 2,4-dichlorobenzyl group, a 2-hydroxybenzyl group, a 3-fluorobenzyl group, a 4-nitrobenzyl group, a 4-bromobenzyl group, a 4-fluorobenzyl group, a 3-nitrobenzyl group, a 4-propylbenzyl group, a 3,5- difuorobenzyl group, a 2-cyanobenzyl group, a 2-acetaminobenzyl group a 4-acetaminobenzyl group, a 4-methoxycarbonylbenzyl group, a 4-dimethylaminobenzyl group, a 4-methoxybenzyl group, a 3-trimethylsilyloxybenzyl group, a 4-trifluoromethylbenzyl group, a 4-butyldimethylsilyloxybenzyl group, a 2-methylthiobenzyl group, a 4-trimethylsilyloxybenzyl group, a 4-methylthiobenzyl group) and a substituted or non-substituted phenylaminocarbonyl group.

The compounds of the present invention are specifically illustrated below.

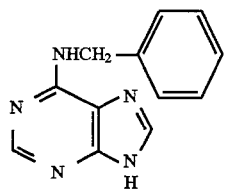
6-benzylaminopurine

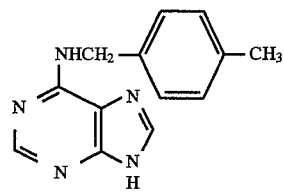
6-(4-methylbenzylamino)purine

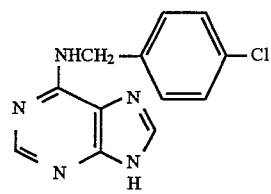
6-(4-chlorobenzylamino)purine

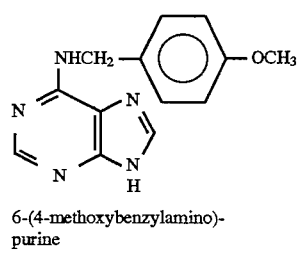
6-(4-methoxybenzylamino)-purine

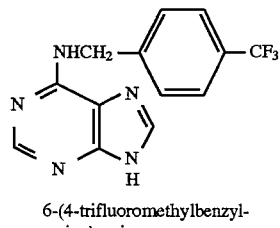
6-(4-trifluoromethylbenzyl-amino)purine

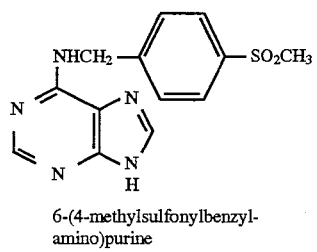
6-(4-methylsulfonylbenzyl-amino)purine

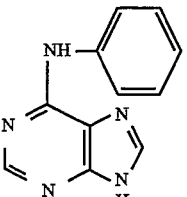
6-phenylaminopurine

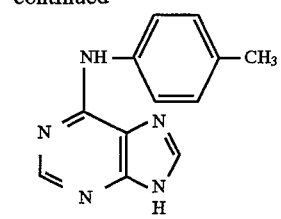
6-(4-methylphenylamino)purine

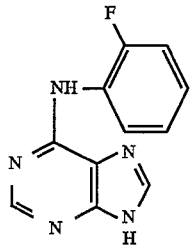
6-(2-fluorophenylamino)-purine

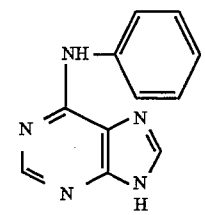
6-(4-cyanophenylamino)purine

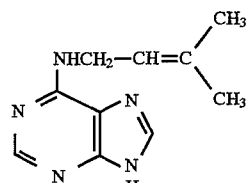
6-(3-methyl-2-butenylamino)-purine

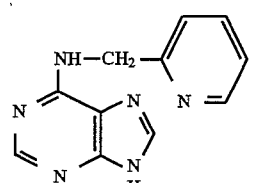
6-(2-pyridylmethylamino)-purine

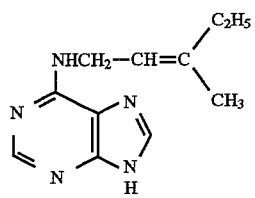
6-(3-methyl-2-pentenylamino)-purine

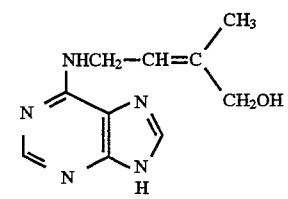
6-(4-hydroxy-3-methyl-2-butenylamino)purine

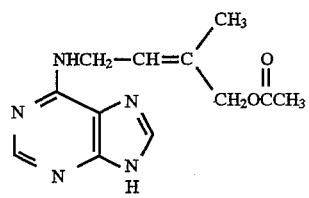
6-(4-acetoxy-3-methyl-2-butenylamino)purine

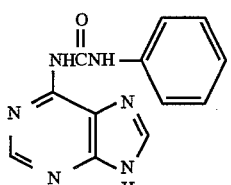
6-(phenylureido)purine

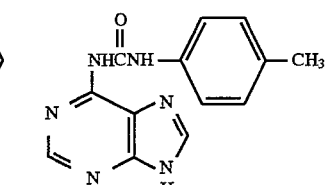
6-(4-methylphenylureido)purine

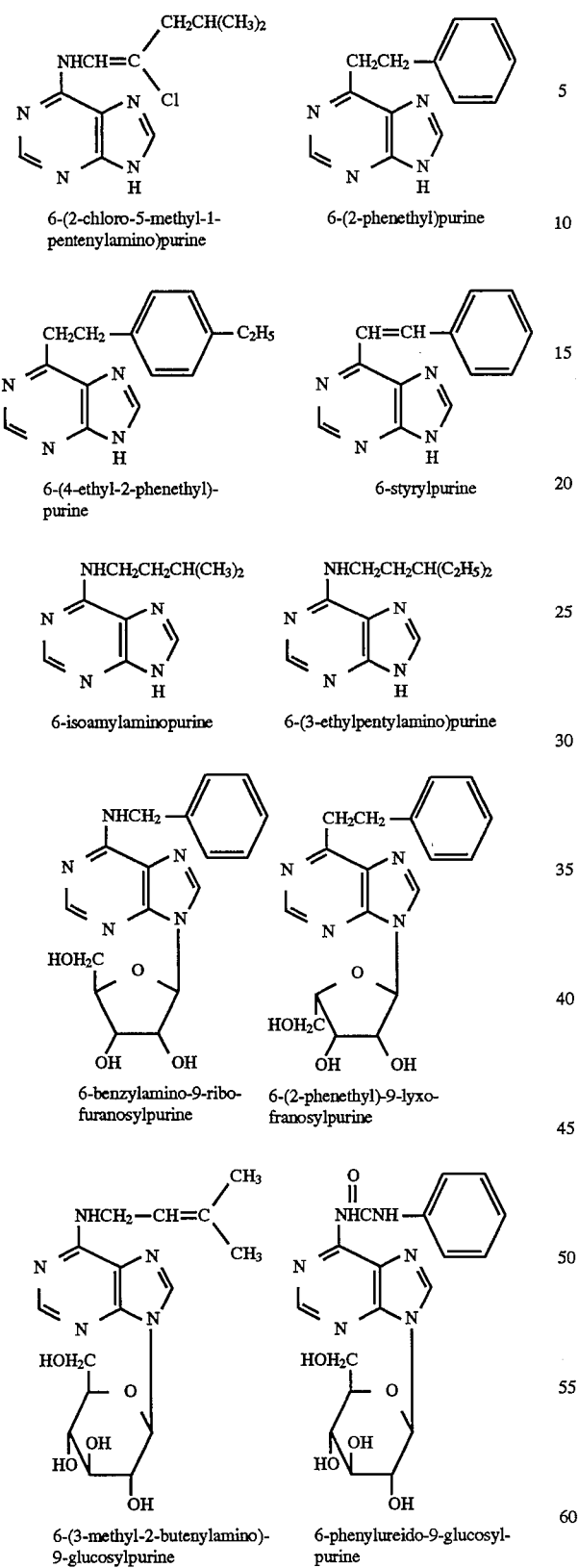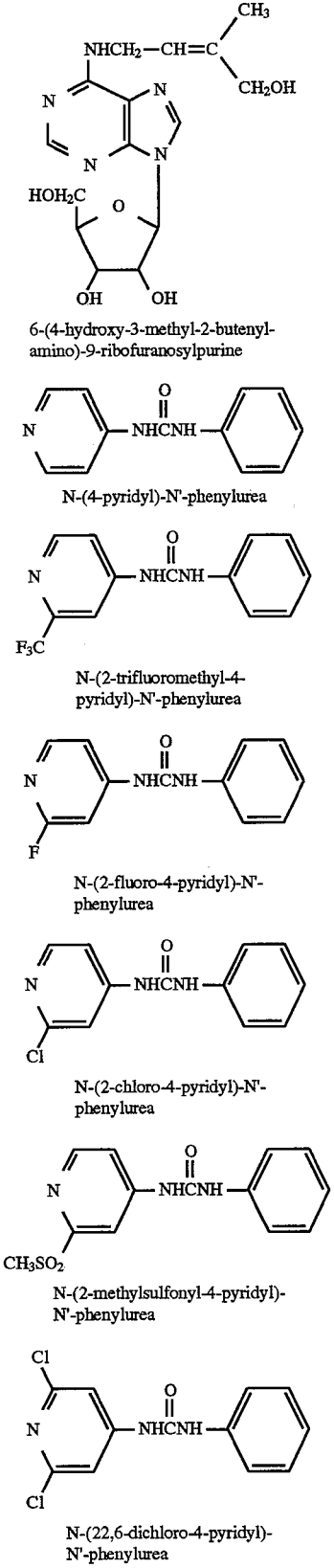

-continued

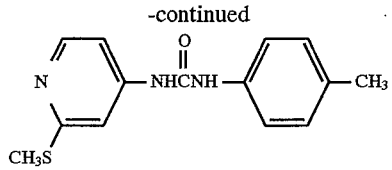

N-(2-methylthio-4-pyridyl)-
N'-(4-methylphenyl)urea

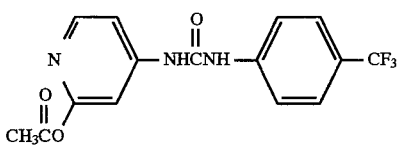

N-(2-acetoxy-4-pyridyl)-N'-
(4-trifluoromethylphenyl)urea

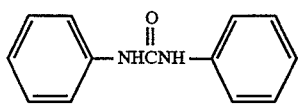

diphenylurea

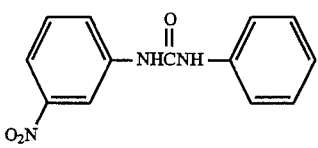

N-(3-nitrophenyl)-N'-phenyl-urea

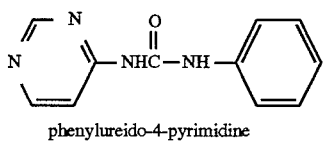

phenylureido-4-pyrimidine

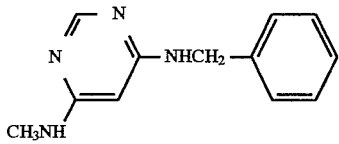

4-benzylamino-6-methylamino-
pyrimidine

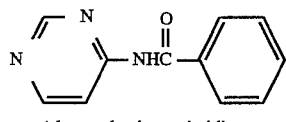

4-benzoylaminopyrimidine

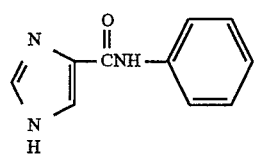

4-imidazolecarbanilide

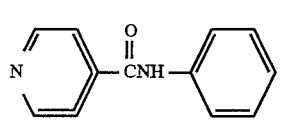

isonicotinic acid anilide

-continued

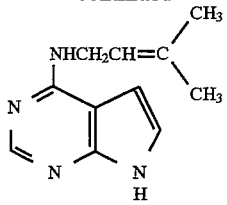

4-(3-methyl-2-butenylamino)-
pyrrolo[2,3-d]pyrimidine

The above-described compounds to be used in the present invention may be obtained as chemically synthesized compounds or as natural products. Extracts containing these compounds may also be used. As the natural products, there are illustrated various parts of various plants, particularly coconuts milk, corn seeds, immature fruits of horse-chestnut (*Aesculus hippocastanum L.*), bananas and apples, roots chicory (*Chichorium intybus L.*), seeds of lupine, and leaves of poplar. Illustrative of the extracts are a hydrolyzate of yeast DNA, an extract of herring spermatozoa and an extract of a culture liquor of fungi, an extract of various transfer RNA and an extract of Corynebacterium fascians.

Of the above-described compounds to be used as effective ingredients in the present invention, those represented by the general formula (1) exhibit particularly remarkable effects. The compounds to be used as effective ingredients may be used independently or may be used in combination of two or more for attaining an enhanced effect of promoting hair growth or curing alopecia such as male alopecia or alopecia areata.

The preparation of the present invention for external use includes a medicine, a quasi-drug and a cosmetic and may be in various known forms which permit external application, such as cream, lotion, emulsion, ointment, gel, hair tonic, hair liquid, liniment, hair rinse, hair shampoo, hair treatment, hair conditioner, aerosol and mousse. As a base for the preparation, any liquid or solid material acceptable for application to hair may be used. If necessary, there may be added to the preparation various additives such as an antiseptic, a perfume, a stabilizing agent, a colorant, an ultraviolet ray absorbent, an antioxidant, a humectant, a thickening agent, etc.

Illustrative of the antiseptic are benzoic acid salts, salicylic acid salts, sorbic acid salts, dehydroacetic acid salts, p-hydroxybenzoic acid esters, 2,4,4'-trichloro-2'-hydroxydiphenyl ether, 3,4,4'-trichlorocarbanide, benzalkonium chloride, hinokitiol, resorcin, ethanol, etc.

Illustrative of the stabilizing agent are chelating agents such as ethylenediaminetetraacetic acid salts, pyrophosphoric acid salts, hexametaphosphoric acid salts, citric acid salts, tartaric acid and gluconic acid and pH-adjusting agents such as sodium hydroxide and potassium hydrogenphosphate.

Illustrative of the ultraviolet ray absorbent are 4-methoxybenzophenone, octyl dimethyl-p-aminobenzoate, ethylhexyl p-methoxycinnamoate, titanium oxide, kaolin and talc.

Illustrative of the anti-oxidant are dibutylhydroxytoluene, butylhydroxyanisole and propyl gallate.

Illustrative of the humectant are polyhydric alcohols (e.g., glycerin, propylene glycol, 1,3-butylene glycol, sorbitol, mannitol, polyethylene glycol and dipropylene glycol), NMF components (e.g., amino acids, sodium lactate and sodium pyrolidonecarboxylate) and water-soluble high-molecular substances (e.g., hyaluronic acid, collagen, elastin, chondroitin sulfate, dermatan sulfate, fibronectin, ceramides, heparin-like materials and chitosan.

Illustrative of the thickening agent are natural high-molecular materials (e.g., sodium alginate, xanthan gum, aluminum silicate, an extract of semen cydnoniae, tragacanth gum and starch), semi-synthetic high-molecular materials (e.g., methyl cellulose, hydroxyethyl cellulose, carboxymethyl cellulose, soluble starch and cationized cellulose) and synthetic high-molecular substances (e.g., carboxyvinyl polymer and polyvinyl alcohol).

As to the amount of the effective ingredient to be contained in the preparation of the present invention may properly be changed depending upon the degree of alopecia and kind of preparation form but, as a general guide, it is contained in an amount of from about 0.0001 to about 20% by weight, preferably from about 0.01 to about 10% by weight, based on the preparation.

The effective ingredients may be used alone or may be used in combination of other known chemicals commonly used as effective ingredients for a preparation for promoting hair growth, such as c-AMP and its derivatives, forskolin, carpronium chloride, pentadecanoic acid glyceride, minoxidil and female sex hormones represented by estradiol, for more enhancing the effect of the present invention of promoting hair growth or curing alopecia such as male alopecia or alopecia areata. In addition, cepharanthine, vitamin A, vitamin E, vitamin E nicotinate, vitamin B group compounds (e.g., nicotinic acid, nicotinic acid amide and benzyl nicotinate), other vitamins (e.g., biotin and pantothenic acid derivatives), vasodilators for peripheral blood vessel (e.g., ginger tincture and capsicum tincture), refrigerants (e.g., camphor and menthol), germicides (e.g., hinokitiol, benzalkonium chloride and undecylenic acid), anti-inflammatory agents (e.g., lysozyme chloride, glycyrrhizin and allantoin), cell-activating agents (e.g., an extract of Japanese chirata, an extract of garlic, an extract of ginseng, an extract of scutellaria, an extract of rosemary, an extract of aloe and an extract of placenta), a photosensitizer, protein kinase C inhibitors (e.g., H-7), an extract of P. japonicus C. A. Mey, and extract of cashew and an extract of malt root may properly be selected to use in combination with the effective ingredients of the present invention.

Formulation examples of the preparations of the present invention for promoting hair growth and test examples demonstrating the advantages of the present invention are described below which, however, are not to be construed as limiting the present invention in any way.

Additionally, the term "proper amount" used in the formulation examples means the amount to make the total 100% by weight.

<Formulation Example 1>
Hair cream

|   | | % by weight |
|---|---|---|
| A | Liquid paraffin | 10.0 |
|   | Squalane | 7.0 |
|   | jojoba oil | 3.0 |
|   | Solid paraffin | 3.0 |
|   | Polyoxyethylene cetyl ether | 2.0 |
|   | Sorbitan sesquioleate | 1.0 |
|   | Potassium hydroxide | 0.1 |
|   | 6-Styrylpurine | 5.0 |
| B | Glycerin | 3.0 |
|   | Ethylparaben | 0.1 |
|   | Purified water | proper amount |

Ingredients belonging to group A were heated to make solution A. Separately, ingredients belonging to group B were heated to make solution B. The solution B was added to the solution A, and the mixture was stirred to emulsify. The resulting emulsion was cooled to prepare a hair cream.

<Formulation Example 2>

Hair tonic

|   |   | % by weight |
|---|---|---|
| A | Polyoxyethylene hydrogenated castor oil | 1.0 |
|   | Ginger tincture | 1.0 |
|   | Isopropylmethylphenol | 0.05 |
|   | Ethanol | 55.0 |
|   | 6-Benzylaminopurine | 0.5 |
| B | Glycerin | 2.0 |
|   | Purified water | proper amount |

Ingredients belonging to group A were uniformly heated to make solution A. Separately, ingredients belonging to group B were uniformly dissolved and gradually added to solution A, followed by uniform stirring to prepare a hair tonic.

<Formulation Example 3>

Hair treatment

|   |   | % by weight |
|---|---|---|
| A | Avocado oil | 5.0 |
|   | Squalane | 5.0 |
|   | Liquid paraffin | 10.0 |
|   | Stearic acid | 3.0 |
|   | Glycerin monostearate | 3.0 |
|   | Hydrous lanolin alcohol | 5.0 |
|   | 6-Benzylamino-9-ribofuranosylpurine | 2.0 |
| B | Extract of Japanese chirata | 1.0 |
|   | 1,3-Butylene glycol | 5.0 |
|   | Triethanolamine | 1.0 |
|   | Methylparaben | 0.2 |
|   | Purified water | proper amount |

Ingredients belonging to group A were heated to make solution A. Separately, ingredients belonging to group B were heated to make solution B. The solution B was added to the solution A, and the mixture was stirred to emulsify. The resulting emulsion was cooled to prepare a hair treatment.

<Formulation Example 4>

Hair shampoo

|   |   | % by weight |
|---|---|---|
| A | Vitamin $B_{12}$ | 0.05 |
|   | N-coconut oil fatty acid-L glutamic acid in triethanolamine (30%) | 40.0 |
|   | Coconut oil fatty acid diethanolamide | 3.0 |
|   | Polyoxyethylene dioleic acid methyl glucoside (120 E.O.) | 2.0 |
|   | N-(2-Chloro-4-pyridyl)-N'-phenylurea | 2.5 |
| B | Ethyl p-hydroxybenzoate | 0.3 |
|   | Disodium edetate | 0.1 |
|   | Purified water | proper amount |

Ingredients belonging to group A were uniformly stirred to make solution A. Separately, ingredients belonging to group B were uniformly heated and dissolved and gradually added to solution A, followed by uniform stirring to prepare a hair shampoo.

<Formulation Example 5>
Aerosol

|   | | % by weight |
|---|---|---|
| A | Benzyl nicotinate | 0.01 |
|   | Vitamin E acetate | 0.05 |
|   | Cetanol | 1.2 |
|   | N-(2-Trifluoromethyl-4-pyridyl)-N'-phenylurea | 0.05 |
|   | 6-(2-Phenethyl)purine | 0.05 |
|   | Propylene glycol | 4.0 |
|   | Ethanol | 8.0 |
|   | Purified water | proper amount |
| B | Liquefied petroleum gas (propellant) | 7.0 |

Ingredients belonging to group A were uniformly mixed to make solution A. The solution A was placed in an aerosol vessel, and the vessel was filled with B in a conventional manner to prepare an aerosol.

<Formulation Example 6>
Air foam

|   | | % by weight |
|---|---|---|
| A | Hinokitiol | 0.1 |
|   | Cetanol | 1.2 |
|   | Propylene glycol | 2.0 |
|   | Dimethylsilicone oil | 2.0 |
|   | Polyoxyethylene hardened castor oil | 2.5 |
|   | Liquid paraffin | 1.0 |
|   | Polyvinylpyrrolidone | 0.5 |
|   | N-(2,6-Dichloro-4-pyridyl)-N'-phenylurea | 3.0 |
|   | Methylparaben | 0.2 |
|   | Ethanol | 10.0 |
|   | Purified water | proper amount |
| B. | Liquefied petroleum gas (propellant) | 4.0 |

Ingredients belonging to group A was uniformly mixed and placed in a vessel. The vessel was filled with component B in a conventional manner to prepare an air foam.

<Formulation Example 7>
Hair liquid

|   | | % by weight |
|---|---|---|
| A | Polyoxypropylene butyl ether (40 P.O.) | 15.0 |
|   | Diisopropanolamine | 0.5 |
|   | 6-(4-Hydroxy-3-methyl-2-butenylamino)-purine | 8.0 |
|   | Ethanol | 50.0 |
| B | Propylene glycol | 3.0 |
|   | Purified water | proper amount |

Ingredients belonging to group A were uniformly stirred at ordinary temperature to make solution A. Separately, ingredients belonging to group B were uniformly dissolved and gradually added to solution A, followed by uniform stirring to prepare a hair liquid.

<Formulation Example 8>
Milk lotion

|   | | % by weight |
|---|---|---|
| A | Polyoxypropylene behenyl ether (20 P.O.) | 0.5 |
|   | Tetraoleic acid polyoxyethylenesorbit (60 E.O.) | 1.0 |
|   | Oleophilic monostearyl glyceride | 1.0 |
|   | Stearic acid | 1.5 |

-continued

|   | | % by weight |
|---|---|---|
|   | Behenyl ether | 1.5 |
|   | Avocado oil | 3.0 |
|   | Natural vitamin E | 0.02 |
|   | 6-Phenylureidopurine | 0.05 |
|   | Diphenylurea | 0.05 |
|   | 6-Benzylaminopurine | 1.0 |
| B | 1,3-Butylene glycol | 5.0 |
|   | Purified water | proper amount |

Ingredients belonging to group A were heated to prepare solution A. Separately, ingredients belonging to group B were heated to prepare solution B. Solution B was added to solution A and emulsified, followed by cooling the emulsion to prepare a milk lotion.

<Test Example 1>
Hair-growing test using mouse (1) Effect of independent application ddY strain white mice (male, 7-week old, 32 g in weight) in a period of telogen with total back hair were clipped from tail to back using a pair of electric fur clippers, and a sample milk lotion prepared by incorporating 1% by weight of the effective ingredient of the present invention in a base of the formulation example 8 was applied to the clipped portion of each mouse on and after the next day of clipping, twice a day and 5 days a week in an amount of 0.2 ml per application to a mouse. Ten mouse were used for one sample.

Hair-growing effect was evaluated by comparing number of mice growing hair and hair-growing area with those of a control group on the 35th day from the start of the test. The hair-growing area was determined by photographing the tested portion, cutting out the hair-growing area of the photograph, and calculating the weight ratio of the cut-out photograph with that before the application, with ten ratios thus calculated as to mice belonging to the same group being averaged.

Additionally, mice of a control group were applied with the base alone, and mice of a positive control group were applied with a 4% pentadecanoic acid glyceride.

Results of the test are tabulated in Table 1.

(2) Effect of combined application

Effect of combined application of the ingredients of the present invention and combined application of the ingredient of the present invention and other known effective ingredient were evaluated according to the above-described independent application. Results thus obtained are shown in Tables 2 to 11.

Additionally, the results with the control of applying only the base were: Number of hair-growing mice: 2/10; Ratio off hair-growing area: 23.1%.

TABLE 1

Results of hair-growing test

| Sample | Number of Hair-growing Mice | Ratio of Hair-growing Area (%) |
|---|---|---|
| Control | 2/10 | 26.3 |
| Pentadecanoic acid glyceride | 6/10 | 61.5 |
| 6-Phenylaminopurine | 7/10 | 70.5 |
| 6-(3-Methyl-2-butenylamino)purine | 8/10 | 71.9 |
| 6-(4-Hydroxy-3-methyl-2-butenylamino)-purine | 6/10 | 65.0 |
| 6-(4-Acetoxy-3-methyl-2-butenylamino)-purine | 6/10 | 64.3 |

TABLE 1-continued

Results of hair-growing test

| Sample | Number of Hair-growing Mice | Ratio of Hair-growing Area (%) |
|---|---|---|
| 6-Benzylaminopurine | 9/10 | 79.1 |
| 6-Phenylureidopurine | 6/10 | 67.8 |
| 6-(2-Chloro-5-methyl-1-pentanylamino)-purine | 8/10 | 74.2 |
| 6-(2-Phenethyl)purine | 7/10 | 69.4 |
| 6-Styrylpurine | 8/10 | 80.7 |
| 6-Isoamylaminopurine | 7/10 | 66.1 |
| 6-Benzylamino-9-ribofuranosylpurine | 7/10 | 67.7 |
| N-(2-Chloro-4-pyridyl)-N'-phenylurea | 7/10 | 66.6 |
| N-(4-Pyridyl)-N'-phenylurea | 7/10 | 66.3 |
| N-(2-Trifluoromethyl-4-pyridyl)-N'-phenylurea | 8/10 | 76.5 |
| N-(2,6-Dichloro-4-pyridyl)-N'-phenylurea | 6/10 | 64.8 |
| 4-Benzylamino-6-methylaminopyrimidine | 7/10 | 70.4 |
| 4-Phenylureidopyrimidine | 6/10 | 65.9 |
| N-(3-Nitrophenyl)-N'-phenylurea | 6/10 | 63.2 |
| 4-Imidazolecarbanilide | 6/10 | 64.7 |
| Isonitotinic acid anilide | 8/10 | 78.1 |
| 4-(3-methyl-2-butenylamino)-pyrrolo-[2,3-d]-pyrimidine | 6/10 | 62.2 |

TABLE 2

Results of hair-growting test

| Ingredient (present invention) | Incorporated Amount (% by weight) Test Sample | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 6-Benzylaminopurin | 0.3 | | | | | | | | | | | |
| 6-(4-Methylbenzylamino)-purine | | 0.3 | | | | | | | | | | |
| 6-Phenylaminopurine | | | 0.3 | | | | | | | | | |
| 6-Styrylaminopurine | | | | 0.3 | | | | | | | | |
| 6-Benzylamino-9-ribofuranosylpurine | | | | | 0.3 | | | | | | | |
| 6-Phenylureidopurine | | | | | | 0.3 | | | | | | |
| 6-(2-Phenethyl)purine | | | | | | | 0.3 | | | | | |
| 6-(3-Methyl-2-butenyl-amino)-9-glycosylpurine | | | | | | | | 0.3 | | | | |
| 6-(4-Methoxybenzyl-amino)purine | | | | | | | | | 0.3 | | | |
| N-(2-Chloro-4-pyridyl)-N'-phenylurea | | | | | | | | | | 0.3 | | |
| N-(2-Trifluoromethyl-4-pyridyl)-N'-phenylurea | | | | | | | | | | | 0.3 | |
| N-(2,6-Dichloro-4-pyridyl-N'-phenylurea | | | | | | | | | | | | 0.3 |
| Number of hair-growing mice | 3/10 | 3/10 | 3/10 | 3/10 | 3/10 | 3/10 | 3/10 | 3/10 | 3/10 | 3/10 | 3/10 | 3/10 |
| Hair-growing area (%) | 38.4 | 39.8 | 37.6 | 38.1 | 35.1 | 34.8 | 36.1 | 35.1 | 37.1 | 32.8 | 31.8 | 29.4 |

TABLE 3

Results of hair-growing test

| Ingredient (present invention) | Incorporated Amount (% by weight) Test Sample | | | | | | | | |
|---|---|---|---|---|---|---|---|---|---|
| | 13 | 14 | 15 | 16 | 17 | 18 | 19 | 20 | 21 |
| 6-Benzylaminopurine | 0.3 | 0.3 | | | | | | | |
| 6-(4-Methylbenzylamino)-purine | 0.3 | | | | | | | | |

TABLE 3-continued

Results of hair-growing test

| Ingredient (present invention) | Incorporated Amount (% by weight) Test Sample | | | | | | | | |
|---|---|---|---|---|---|---|---|---|---|
| | 13 | 14 | 15 | 16 | 17 | 18 | 19 | 20 | 21 |
| 6-Phenylaminopurine | | 0.3 | | | | | | | |
| 6-Styrylaminopurine | | | 0.3 | | | | | | |
| 6-Benzylamino-9-ribo-furanosylpurine | | | 0.3 | 0.3 | | | | | |
| 6-Phenylureidopurine | | | | 0.3 | 0.3 | | | | |
| 6-(2-Phenethyl)purine | | | | | | 0.3 | 0.3 | | |
| 6-(3-Methyl-2-butenyl-amino)-9-glycosylpurine | | | | | | | | 0.3 | |
| 6-(4-Methoxybenzyl-amino)purine | | | | | 0.3 | | | | 0.3 |
| N-(2-Chloro-4-pyridyl)-N'-phenylurea | | | | | | 0.3 | 0.3 | | |
| N-(2-Trifluoromethyl-4-pyridyl)-N'-phenylurea | | | | | | | | 0.3 | |
| N-(2,6-Dichloro-4-pyridyl-N'-phenylurea | | | | | | | | | 0.3 |
| Number of hair-growing mice | 8/10 | 8/10 | 7/10 | 6/10 | 7/10 | 7/10 | 6/10 | 7/10 | 7/10 |
| Hair-growing area (%) | 83.1 | 78.1 | 75.3 | 69.8 | 72.7 | 73.1 | 69.4 | 70.3 | 75.4 |

TABLE 4

Results of hair-growing test

| Ingredient (present invention) | Incorporated Amount (% by weight) Test Sample | | | | | | | | | | | |
|---|---|---|---|---|---|---|---|---|---|---|---|---|
| | 1 | 22 | 3 | 4 | 5 | 8 | 10 | 23 | 24 | 25 | 26 | 27 |
| 6-Benzylaminopurine | 0.3 | | | | | | | | | | | |
| 6-(4-Methoxybenzyl-aminopurine | | 0.3 | | | | | | | | | | |
| 6-Phenylaminopurine | | | 0.3 | | | | | | | | | |
| 6-Styrylaminopurine | | | | 0.3 | | | | | | | | |
| 6-Benzylamino-9-ribo-furanosylpurine | | | | | 0.3 | | | | | | | |
| 6-(3-Methyl-2-butenyl-amino)-9-glucosylpurine | | | | | | 0.3 | | | | | | |
| N-(2-Chloro-4-pyridyl)-N'-phenylurea | | | | | | | 0.3 | | | | | |
| Diphenylurea | | | | | | | | 0.3 | | | | |
| Phenylureido-4-pyrimidine | | | | | | | | | 0.3 | | | |
| 4-Imidazolecarbanide | | | | | | | | | | 0.3 | | |
| Isonicotinic acid anilide | | | | | | | | | | | 0.3 | |
| 4-(3-Methyl-2-butenyl-amino)pyrrolo[2,3-d]-pyrimidine | | | | | | | | | | | | 0.3 |
| Number of hair-growing mice | 3/10 | 3/10 | 3/10 | 3/10 | 3/10 | 3/10 | 3/10 | 3/10 | 3/10 | 3/10 | 3/10 | 3/10 |
| Hair-growing area (%) | 38.4 | 39.8 | 37.6 | 38.1 | 35.1 | 31.4 | 32.8 | 32.9 | 30.1 | 32.4 | 29.8 | 28.7 |

TABLE 5

Results of hair-growing test

| Ingredient (present invention) | Incorporated Amount (% by weight) Test Sample | | | | | | | | |
|---|---|---|---|---|---|---|---|---|---|
| | 28 | 29 | 30 | 31 | 32 | 33 | 34 | 35 | 36 |
| 6-Benzylaminopurine | 0.3 | 0.3 | | | | | | | |
| 6-(4-Methoxybenzyl-aminopurine | | | 0.3 | 0.3 | | | | | |
| 6-Phenylaminopurine | | | | | 0.3 | | | | |
| 6-Styrylaminopurine | | | | | | 0.3 | | | |
| 6-Benzylamino-9-ribo-furanosylpurine | | | | | | | 0.3 | | |
| 6-(3-Methyl-2-butenyl-amino)-9-glucosylpurine | | | | | | | | 0.3 | |
| N-(2-Chloro-4-pyridyl)-N'-phenylurea | 0.3 | | | | | | | | 0.3 |
| Diphenylurea | | 0.3 | | | 0.3 | | | | |
| Phenylureido-4-pyrimi-dine | | | 0.3 | | | 0.3 | | | |
| 4-Imidazolecarbanide | | | | 0.3 | | | 0.3 | | |
| Isonicotinic acid anilide | | | | | | | | 0.3 | |
| 4-(3-Methyl-2-butenyl-amino)pyrrolo[2,3-d]-pyrimidine | | | | | | | | | 0.3 |
| Number of hair-growing mice | 7/10 | 7/10 | 6/10 | 6/10 | 7/10 | 6/10 | 7/10 | 6/10 | 6/10 |
| Hair-growing area (%) | 76.5 | 78.1 | 68.9 | 67.4 | 71.4 | 70.3 | 77.3 | 70.4 | 67.8 |

TABLE 6

Results of hair-growing test

| Ingredient | Incorporated Amount (% by weight) Test Sample | | | | | | | | |
|---|---|---|---|---|---|---|---|---|---|
| | 1 | 2 | 3 | 4 | 5 | 6 | 7 | 8 | 9 |
| 6-Benzylaminopurine* | 0.3 | | | | | | | | |
| 6-(4-Methylbenzyl-amino)purine* | | 0.3 | | | | | | | |
| Dibutyl c-AMP** | | | 0.5 | | | | | | |
| Forskolin** | | | | 0.5 | | | | | |
| Carpronium chloride** | | | | | 0.5 | | | | |
| Pentadecanoic acid glyceride** | | | | | | 2.0 | | | |
| Capticum tincture** | | | | | | | 0.1 | | |
| Japanese chirata extract** | | | | | | | | 0.1 | |
| Ginseng extract** | | | | | | | | | 0.1 |
| Number of hair-growing mice | 3/10 | 3/10 | 2/10 | 2/10 | 2/10 | 2/10 | 2/10 | 2/10 | 2/10 |
| Hair-growing area (%) | 38.4 | 39.8 | 32.1 | 30.1 | 30.8 | 28.6 | 22.7 | 25.8 | 27.4 |

*Ingredient of the present invention
**Ingredient used in combination with the ingredient of the present invention

TABLE 7 (A)

Results of hair-growing test

| Ingredient | Incorporated Amount (% by weight) Test Sample | | | | | |
|---|---|---|---|---|---|---|
| | 10 | 11 | 12 | 13 | 14 | 15 |
| 6-Benzylaminopurine* | 0.3 | 0.3 | 0.3 | 0.3 | 0.3 | 0.3 |
| 6-(4-Methylbenzyl-amino)purine* | | | | | | |
| Dibutyl c-AMP** | 0.5 | | | | | |
| Forskolin** | | 0.5 | | | | |
| Carpronium chloride** | | | 0.5 | | | |
| Pentadecanoic acid glyceride** | | | | 2.0 | | |
| Capticum tincture** | | | | | 0.1 | |
| Japanese chirata | | | | | | 0.1 |

TABLE 7 (A)-continued

Results of hair-growing test

| | Incorporated Amount (% by weight) Test Sample | | | | | |
|---|---|---|---|---|---|---|
| Ingredient | 10 | 11 | 12 | 13 | 14 | 15 |
| extract** | | | | | | |
| Ginseng extract** | | | | | | |
| Number of hair-growing mice | 9/10 | 9/10 | 9/10 | 9/10 | 8/10 | 8/10 |
| Hair-growing area (%) | 89.1 | 90.3 | 91.5 | 88.7 | 86.5 | 84.3 |

*Ingredient of the present invention
**Ingredient used in combination with the ingredient of the present invention

TABLE 7 (B)

Results of hair-growing test

| | Incorporated Amount (% by weight) Test Sample | | | | | |
|---|---|---|---|---|---|---|
| Ingredient | 16 | 17 | 18 | 19 | 20 | 21 |
| 6-Benzylaminopurine* | | | | | | |
| 6-(4-Methylbenzyl-amino)purine* | 0.3 | 0.3 | 0.3 | 0.3 | 0.3 | 0.3 |
| Dibutyl c-AMP** | 0.5 | | | | | |
| Forskolin** | | 0.5 | | | | |
| Carpronium chloride** | | | | | | |
| Pentadecanoic acid glyceride** | | | 0.2 | | | |
| Capticum tincture** | | | | 0.1 | | |
| Japanese chirata extract** | | | | | 0.1 | |
| Ginseng extract** | | | | | | 0.1 |

TABLE 7 (B)-continued

Results of hair-growing test

| | Incorporated Amount (% by weight) Test Sample | | | | | |
|---|---|---|---|---|---|---|
| Ingredient | 16 | 17 | 18 | 19 | 20 | 21 |
| Number of hair-growing mice | 9/10 | 9/10 | 9/10 | 8/10 | 8/10 | 8/10 |
| Hair-growing area (%) | 90.3 | 89.1 | 90.4 | 87.2 | 84.6 | 85.7 |

*Ingredient of the present invention
**Ingredient used in combination with the ingredient of the present invention

TABLE 8

Results of hair-growing test

| | Incorporated Amount (% by weight) Test Sample | | | | | | | | | |
|---|---|---|---|---|---|---|---|---|---|---|
| Ingredient | 22 | 23 | 24 | 25 | 6 | 5 | 8 | 26 | 7 | 27 |
| 6-Phenylaminopurine* | 0.3 | | | | | | | | | |
| 6-Styrylpurine* | | 0.3 | | | | | | | | |
| 6-Benzylamino-9-ribo-furanosylpurine* | | | 0.3 | | | | | | | |
| Minoxidil** | | | | 0.5 | | | | | | |
| Pentadecanoic acid glyceride** | | | | | 0.5 | | | | | |
| Carpronium chloride** | | | | | | 0.5 | | | | |
| Japanese chirata extract** | | | | | | | 0.1 | | | |
| Estradiol** | | | | | | | | 0.5 | | |
| Capticum tincture** | | | | | | | | | 0.1 | |
| Ginger extract** | | | | | | | | | | 0.1 |
| Number of hair-growing mice | 3/10 | 3/10 | 3/10 | 2/10 | 2/10 | 2/10 | 2/10 | 2/10 | 2/10 | 2/10 |
| Hair-growing area (%) | 37.6 | 38.1 | 35.1 | 28.1 | 28.6 | 30.8 | 25.8 | 25.9 | 22.7 | 26.1 |

*Ingredient of the present invention
**Ingredient used in combination with the ingredient of the present invention

TABLE 9

Results of hair-growing test

| Ingredient | Incorporated Amount (% by weight) Test Sample | | | | | | | | | | |
|---|---|---|---|---|---|---|---|---|---|---|---|
| | 28 | 29 | 30 | 31 | 32 | 33 | 34 | 35 | 36 | 37 | 38 |
| 6-Phenylaminopurine* | 0.3 | 0.3 | 0.3 | 0.3 | | | | | | | |
| 6-Styrylpurine* | | | | | 0.3 | 0.3 | 0.3 | | | | |
| 6-Benzylamino-9-ribo-furanosylpurine* | | | | | | | | 0.3 | 0.3 | 0.3 | 0.3 |
| Minoxidil** | 0.5 | | | | 0.5 | | | | | | |
| Pentadecanoic acid glyceride** | | 0.2 | | | 2.0 | | 2.0 | | | | |
| Carpronium chloride** | | | | | | | | 0.5 | | | |
| Japanese chirata extract** | | | 0.1 | | | | | | | | |
| Estradiol** | | | | 0.5 | | | | | 0.5 | | |
| Capticum tincture** | | | | | | 0.1 | | | | | |
| Ginger extract** | | | | | | | | | | | 0.1 |
| Number of hair-growing mice | 9/10 | 8/10 | 8/10 | 8/10 | 9/10 | 9/10 | 8/10 | 9/10 | 9/10 | 8/10 | 8/10 |
| Hair-growing area (%) | 89.5 | 82.1 | 83.6 | 84.9 | 90.3 | 91.5 | 84.5 | 89.7 | 90.5 | 86.5 | 87.8 |

*Ingredient of the present invention
**Ingredient used in combination with the ingredient of the present invention

TABLE 10 (A)

Results of hair-growing test

| Ingredient | Incorporated Amount (% by weight) Test Sample | | | | | |
|---|---|---|---|---|---|---|
| | 39 | 40 | 41 | 42 | 43 | 44 |
| N-(2-Chloro-4-pyrid-yl)-N'-phenylurea* | 0.3 | | | | | |
| Diphenylurea* | | 0.3 | | | | |
| Phenylureido-4-pyrimidine* | | | 0.3 | | | |
| 4-Imidaaolecarbanilide* | | | | 0.3 | | |
| Isonicotinic acid anilide* | | | | | 0.3 | |
| 4-(3-Methyl-2-butenyl-amino)pyrrolo[2,3-d]-pyrimidine* | | | | | | 0.3 |
| Number of hair-growing mice | 3/10 | 3/10 | 3/10 | 3/10 | 3/10 | 3/10 |
| Hair-growing area (%) | 32.8 | 33.9 | 31.9 | 34.3 | 32.8 | 33.9 |

*Ingredient of the present invention

TABLE 10 (B)

Results of hair-growing test

| Ingredient | Incorporated Amount (% by weight) Test Sample | | | | | |
|---|---|---|---|---|---|---|
| | 25 | 5 | 6 | 26 | 7 | 8 |
| Minoxidil** | 0.5 | | | | | |
| Carpronium chloride** | | 0.5 | | | | |
| Pentadecanoic acid glyceride** | | | 2.0 | | | |
| Estradiol** | | | | 0.5 | | |
| Capticum tincture** | | | | | 0.1 | |
| Japanese chirata extract** | | | | | | 0.1 |
| Number of hair-growing mice | 2/10 | 2/10 | 2/10 | 2/10 | 2/10 | 2/10 |
| Hair-growing area (%) | 28.1 | 30.8 | 28.6 | 25.9 | 22.7 | 256.8 |

**Ingredient used in combination with the ingredient of the present invention

TABLE 11

| | Results of hair-growing test | | | | | | | | |
|---|---|---|---|---|---|---|---|---|---|
| | Incorporated Amount (% by weight) Test Sample | | | | | | | | |
| Ingredient | 45 | 46 | 47 | 48 | 49 | 50 | 51 | 52 | 53 |
| N-(2-Chloro-4-pyridyl)-N'-phenylurea* | 0.3 | 0.3 | | | | | | | |
| Diphenylurea* | | | 0.3 | 0.3 | | | | | |
| Phenylureido-4-pyrimidine* | | | | | 0.3 | 0.3 | | | |
| 4-Imidaaolecarbanilide* | | | | | | | 0.3 | | |
| Isonicotinic acid anilide* | | | | | | | | 0.3 | |
| 4-(3-Methyl-2-butenyl-amino)pyrrolo[2,3-d]-pyrimidine* | | | | | | | | | 0.3 |
| Minoxidil* | 0.5 | | 0.5 | | | | | | |
| Carpronium chloride** | | 0.5 | | | 0.5 | | | | |
| Pentadecanoic acid glyceride** | | | | 2.0 | | 2.0 | | | |
| Estradiol** | | | | | | | 0.5 | | |
| Capticum tincture** | | | | | | | | 0.1 | |
| Japanese chirata extract** | | | | | | | | | 0.1 |
| Number of hair-growing mice | 7/10 | 6/10 | 7/10 | 6/10 | 6/10 | 6/10 | 7/10 | 7/10 | 6/10 |
| Hair growing area (%) | 76.8 | 69.3 | 75.9 | 69.8 | 67.3 | 70.4 | 71.8 | 73.9 | 69.6 |

*Ingredient of the present invention
**Ingredient used in combination with the ingredient of the present invention As is demonstrated above, the ingredients of the present invention show a remarkable effect of promoting hair growth.

<Test Example 2>
Clinical test

Results of clinical test on the curing effect of the ingredients of the present invention for male alopecia.

1) Preparation of samples

Test samples were prepared by respectively incorporating 13 effective ingredients of the present invention of 6-styrylpurine, 6-benzylaminopurine, 6-benzylamino-9-ribofuranosylpurine, N-(2-chloro-4-pyridyl)-N'-phenylurea, N-(2-trifluoromethyl-4-pyridyl)-N'-phenylurea, N-(2,6-dichloro-4-pyridyl)-N'-phenylures, 6-(4-methylbenzylamino)purine, 6-(4-methoxybenzyl-amino) purine, 6-(4-methylsulfonylbenzylamino)purine, 6-phenylureidopurine, 6-(2-phenethyl)purine, diphenylurea and phenylureido-4-pyrimidine in the preparation of formulation example 2 (base) in an amount of 0.5%. Control samples were prepared by using only a base or by respectively incorporating pentadecanoic acid glyceride and carpronium chloride in an amount of 1%.

2) Subjects 480 male volunteers suffering from alopecia were selected and grouped at random into 16 groups each of which were composed of 30 subjects.

3) Testing method

A suitable amount of each sample preparation was applied to the head ranging from the front portion of the head to the top portion thereof twice a day (morning and night) for 4 months.

4) Evaluation of curing effect

Upon completion of the application over four months, hair condition (degree of epilation, sprouting of fine soft hair, change in hair quality) was examined in comparison with that before application by reference to photographic pictures in 5 grades (A: remarkably improved; B: middlingly improved; C: slightly improved; D: no changes; E: changes for the worse). As to side effects, scalp was checked for ruber, pimple and like abnormality after the 4-month application.

5) Standard of evaluation (1) Degree of epilation

A: Epilation was scarcely observed, thus alopecia being overcome.

B: Epilation was considerably reduced.

C: Epilation was slightly reduced.

D: Epilation was not reduced at all.

E: Epilcation was increased.

(2) Growing of fine soft hair

A: Extremely many fine soft hairs were observed to grow.

B: Considerably many fine soft hairs were observed to grow.

C: Fine soft hairs were observed to slightly sprout.

D: Growing of fine soft hair was not observed at all.

E: Fine soft hairs were observed to decrease in number.

(3) Change in hair quality

A: Soft hairs were scaresely observed, thus hair condition being normalized as to hair quality.

B: Soft hairs were made considerably harder.

C: Soft hairs were made slightly harder.

D: No changes were found as to hair quality.

E: Soft hairs increased in number.

(5) Results

Results tabulated in the following Tables 12 to 14 were obtained.

TABLE 12

Degree of epilation

| Incorporated Effective Ingredient | A | B | C | D | E | Side Effect | Total | Improved Ratio (%) |
|---|---|---|---|---|---|---|---|---|
| 6-Styrylpurine* | 11 | 9 | 7 | 3 | 0 | 0 | 30 | 67 |
| 6-Benzylaminopurine* | 14 | 9 | 5 | 2 | 0 | 0 | 30 | 77 |
| 6-Benzylamino-9-ribofuranosylpurine* | 11 | 12 | 4 | 3 | 0 | 0 | 30 | 77 |
| N-(2-Chloro-4-pyridyl)-N'-phenylurea* | 10 | 13 | 6 | 1 | 0 | 0 | 30 | 77 |
| N-(2-Trifluoromethyl-4-pyridyl)-N'-phenylurea* | 12 | 4 | 10 | 4 | 0 | 0 | 30 | 53 |
| N-(2,6-Dichloro-4-pyridyl)-N'-phenylurea* | 14 | 8 | 5 | 3 | 0 | 0 | 30 | 73 |
| 6-(4-Methylbenzylamino)purine* | 11 | 10 | 4 | 5 | 0 | 0 | 30 | 70 |
| 6-(4-Methoxybenzylamino)purine* | 12 | 10 | 5 | 3 | 0 | 0 | 30 | 73 |
| 6-(4-Methylsulfonylbenzylamino)purine* | 11 | 11 | 3 | 5 | 0 | 0 | 30 | 73 |
| 6-Phenylureidopurine* | 10 | 9 | 4 | 7 | 0 | 0 | 30 | 63 |
| 6-(2-Phenethyl)purine* | 10 | 8 | 5 | 7 | 0 | 0 | 30 | 60 |
| Diphenylurea* | 4 | 12 | 8 | 6 | 0 | 0 | 30 | 53 |
| Phenylureido-4-pyrimidine* | 5 | 11 | 6 | 8 | 0 | 0 | 30 | 53 |
| Base ingredients alone** | 0 | 0 | 3 | 25 | 0 | 0 | 30 | 0 |
| Pentadecanoic acid Glyceride** | 2 | 12 | 7 | 9 | 0 | 0 | 30 | 47 |
| Carpronium chloride** | 0 | 2 | 16 | 12 | 0 | 1 | 30 | 7 |

*Group of tested ingredients of the present invention
**Group of control
Note: Numerals in the above table designate numbers of subjects. Improved ratio is a ratio of number of subjects scored A and B to the total number of 30.

TABLE 13

Growing of soft hair

| Incorporated Effective Ingredient | A | B | C | D | E | Side Effect | Total | Improved Ratio (%) |
|---|---|---|---|---|---|---|---|---|
| 6-Styrylpurine* | 13 | 7 | 8 | 2 | 0 | 0 | 30 | 67 |
| 6-Benzylaminopurine* | 15 | 10 | 4 | 1 | 0 | 0 | 30 | 83 |
| 6-Benzylamino-9-ribofuranosylpurine* | 12 | 13 | 3 | 3 | 0 | 0 | 30 | 83 |
| N-(2-Chloro-4-pyridyl)-N'-phenylurea* | 11 | 8 | 10 | 1 | 0 | 0 | 30 | 63 |
| N-(2-Trifluoromethyl-4-pyridyl)-N'-phenylurea* | 8 | 16 | 6 | 0 | 0 | 0 | 30 | 80 |
| N-(2,6-Dichloro-4-pyridyl)-N'-phenylurea* | 8 | 14 | 7 | 1 | 0 | 0 | 30 | 73 |
| 6-(4-Methylbenzylamino)purine* | 11 | 10 | 7 | 2 | 0 | 0 | 30 | 70 |
| 6-(4-Methoxybenzylamino)purine* | 10 | 10 | 7 | 3 | 0 | 0 | 30 | 67 |
| 6-(4-Methylsulfonylbenzylamino)purine* | 10 | 12 | 7 | 1 | 0 | 0 | 30 | 73 |
| 6-Phenylureidopurine* | 9 | 10 | 4 | 7 | 0 | 0 | 30 | 63 |
| 6-(2-Phenethyl)purine* | 10 | 9 | 5 | 6 | 0 | 0 | 30 | 63 |
| Diphenylurea* | 5 | 12 | 4 | 9 | 0 | 0 | 30 | 57 |
| Phenylureido-4-pyrimidine* | 5 | 13 | 4 | 8 | 0 | 0 | 30 | 60 |
| Base ingredients alone** | 0 | 0 | 2 | 28 | 0 | 0 | 30 | 0 |

TABLE 13-continued

Growing of soft hair

| Incorporated Effective Ingredient | A | B | C | D | E | Side Effect | Total | Improved Ratio (%) |
|---|---|---|---|---|---|---|---|---|
| Pentadecanoic acid Glyceride** | 3 | 13 | 2 | 12 | 0 | 0 | 30 | 53 |
| Carpronium chloride** | 1 | 4 | 10 | 15 | 0 | 1 | 30 | 17 |

*Group of tested ingredients of the present invention
**Group of control
Note: Numerals in the above table designate numbers of subjects. Improved ratio is a ratio of number of subjects scored A and B to the total number of 30.

TABLE 14

Change in hair quality

| Incorporated Effective Ingredient | A | B | C | D | E | Side Effect | Total | Improved Ratio (%) |
|---|---|---|---|---|---|---|---|---|
| 6-Styrylpurine* | 11 | 12 | 8 | 1 | 0 | 0 | 30 | 77 |
| 6-Benzylaminopurine* | 14 | 6 | 7 | 3 | 0 | 0 | 30 | 67 |
| 6-Benzylamino-9-ribo-furanosylpurine* | 13 | 5 | 9 | 3 | 0 | 0 | 30 | 60 |
| N-(2-Chloro-4-pyridyl)-N'-phenylurea* | 9 | 6 | 13 | 2 | 0 | 0 | 30 | 50 |
| N-(2-Trifluormethyl-4-pyridyl)-N'-phenyl-urea* | 10 | 7 | 12 | 1 | 0 | 0 | 30 | 57 |
| N-(2,6-Dichloro-4-pyridyl)-N'-phenyl-urea* | 14 | 6 | 5 | 5 | 0 | 0 | 30 | 67 |
| 6-(4-Methylbenzyl-amino)purine* | 11 | 7 | 8 | 4 | 0 | 0 | 30 | 60 |
| 6-(4-Methoxybenzyl-amino)purine* | 10 | 9 | 8 | 3 | 0 | 0 | 30 | 63 |
| 6-(4-Methylsulfonyl-benzylamino)purine* | 9 | 9 | 7 | 5 | 0 | 0 | 30 | 60 |
| 6-Phenylureidopurine* | 8 | 10 | 8 | 4 | 0 | 0 | 30 | 60 |
| 6-(2-Phenethyl)purine* | 7 | 11 | 6 | 6 | 0 | 0 | 30 | 60 |
| Diphenylurea* | 6 | 11 | 6 | 7 | 0 | 0 | 30 | 57 |
| Phenylureido-4-pyrimidine* | 5 | 12 | 7 | 6 | 0 | 0 | 30 | 57 |
| Base ingredients alone** | 0 | 0 | 4 | 23 | 3 | 0 | 30 | 0 |
| Pentadecanoic acid Glyceride** | 3 | 12 | 7 | 8 | 0 | 0 | 30 | 50 |
| Carpronium chloride** | 0 | 4 | 15 | 10 | 1 | 1 | 30 | 17 |

*: Group of tested ingredients of the present invention
**: Group of control
Note:
Numerals in the above table designate numbers of subjects. Improved ratio is a ratio of number of subjects scored A and B to the total number of 30.

As is shown above, the ingredients of the present invention exhibited better effect of curing alopecia than the control ingredients.

The preparation of the present invention for promoting hair growth exhibits an excellent effect of promoting hair growth or curing alopecia such as male alopecia or alopecia areata and can be applied to scalp for prophylaxis of alopecia and curing various alopecia diseases with no serious side effects.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method for growing hair in a male affected with alopecia which comprises administering to the scalp of the male a preparation consisting essentially of about 0.0001 to about 20% by weight of 6-benzylaminopurine.

* * * * *